(12) United States Patent
Kuehner et al.

(10) Patent No.: US 8,679,143 B2
(45) Date of Patent: Mar. 25, 2014

(54) APPLIANCE FOR WATER-JET SURGERY

(75) Inventors: Ralf Kuehner, Stuttgart (DE); Martin Hagg, Wannweil (DE); Stefanie Schmidt, Pliezhausen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 785 days.

(21) Appl. No.: 10/599,672

(22) PCT Filed: Mar. 18, 2005

(86) PCT No.: PCT/EP2005/002917
§ 371 (c)(1),
(2), (4) Date: Oct. 5, 2006

(87) PCT Pub. No.: WO2005/099595
PCT Pub. Date: Oct. 27, 2005

(65) Prior Publication Data
US 2008/0221602 A1    Sep. 11, 2008

(30) Foreign Application Priority Data

Apr. 7, 2004 (DE) .................... 10 2004 017 261
Apr. 29, 2004 (DE) .................... 10 2004 021 035

(51) Int. Cl.
*A61B 17/32* (2006.01)
(52) U.S. Cl.
USPC ........................................... 606/167
(58) Field of Classification Search
USPC ............ 604/150–154, 22, 48, 19, 93.01, 131;
606/159, 167; 417/269–273, 514–516,
417/466–469, 462, 463, 413.1, 413.25, 425,
417/426, 435, 444, 445, 423.14, 533, 2, 8,
417/62, 216, 286, 529, 521, 522, 539;
222/325–327, 385, 386, 372, 380, 526,
222/531, 532, 172; 600/432, 158, 159;
141/22, 26–29; 239/381
See application file for complete search history.

(56) References Cited

U.S. PATENT DOCUMENTS

| | | | | |
|---|---|---|---|---|
| 3,983,864 A | * | 10/1976 | Sielaff et al. | 600/364 |
| 4,109,653 A | * | 8/1978 | Kozam et al. | 604/191 |
| 4,820,272 A | * | 4/1989 | Palmer | 604/110 |
| 5,019,045 A | * | 5/1991 | Lee | 604/110 |
| 5,116,313 A | * | 5/1992 | McGregor | 604/70 |

(Continued)

FOREIGN PATENT DOCUMENTS

| | | |
|---|---|---|
| DE | 3441 054 A2 | 5/1985 |
| DE | 690 25 948 T2 | 12/1996 |

(Continued)

Primary Examiner — Thomas McEvoy
Assistant Examiner — Jocelin Tanner
(74) Attorney, Agent, or Firm — Dickstein Shapiro LLP

(57) ABSTRACT

An appliance for water-jet surgery is provided that includes a plurality of supply cylinder and piston arrangements in each of which is stored a working fluid that can be expelled, by means of the piston, through an outlet into a pressure conduit. At least one actuation device is provided to actuate the piston of each supply cylinder. By means of a change-over device to change the actuation from the piston of one supply cylinder to the piston of another supply cylinder, it is ensured that the working fluid can be expelled into the pressure conduit from consecutively emptying supply cylinders. As a result, an apparatus with a small structure that is achieved by simple means is disclosed.

13 Claims, 5 Drawing Sheets

(56) References Cited

U.S. PATENT DOCUMENTS

| | | | |
|---|---|---|---|
| 5,364,240 A * | 11/1994 | Salecker | 417/427 |
| 5,562,692 A * | 10/1996 | Bair | 606/167 |
| 5,620,414 A | 4/1997 | Campbell, Jr. | |
| 5,916,197 A * | 6/1999 | Reilly et al. | 604/151 |
| 6,216,573 B1 * | 4/2001 | Moutafis et al. | 83/177 |
| 6,994,127 B2 * | 2/2006 | Neracher | 141/27 |
| 7,063,713 B1 | 6/2006 | Butsch et al. | |
| 2002/0177802 A1 * | 11/2002 | Moutafis et al. | 604/22 |
| 2003/0009132 A1 * | 1/2003 | Schwartz et al. | 604/152 |
| 2003/0171670 A1 * | 9/2003 | Gumb et al. | 600/411 |
| 2003/0176833 A1 * | 9/2003 | Libermann | 604/65 |
| 2004/0019313 A1 * | 1/2004 | Childers et al. | 604/5.01 |
| 2004/0055662 A1 | 3/2004 | Neracher | |

FOREIGN PATENT DOCUMENTS

| | | |
|---|---|---|
| DE | 695 09 477 T2 | 11/1999 |
| DE | 199 04 640 A1 | 8/2000 |
| EP | 0 551 920 B1 | 8/1997 |
| GB | 1 402 632 | 8/1975 |
| JP | 2-185261 A | 7/1990 |
| JP | 8-58856 A | 3/1996 |
| WO | WO 95/34333 | 12/1995 |
| WO | 96/39952 A1 | 12/1996 |
| WO | WO 00/45719 | 8/2000 |
| WO | 02/07798 A2 | 1/2002 |
| WO | WO 02/07798 A2 | 1/2002 |

\* cited by examiner

APPLIANCE FOR WATER-JET SURGERY

CROSS-REFERENCE TO RELATED APPLICATIONS

This application is a Section 371 of International Application No. PCT/EP2005/002917, filed Mar. 18, 2005, which was published in the German language on Oct. 27, 2005, under International Publication No. WO 2005/099595 A1 and the disclosure of which is incorporated herein by reference.

FIELD OF THE INVENTION

The disclosed embodiments relate to an appliance for water jet surgery, in which a fluid is expelled from a nozzle under high pressure for the selective cutting of tissue.

BACKGROUND

Customarily in the case of such an appliance a supply cylinder having an (initially closed) outlet at one end is filled with a working fluid, such as Ringer solution, and at its other end is closed by means of a piston. This supply cylinder is then inserted into a stably positioned chamber in an appliance housing. After closure of the housing an actuating rod driven by a hydraulic cylinder is placed in contact with the piston in the supply cylinder. Now the known appliance is ready for operation. During operation the pressure that must be applied to the fluid is generated by the hydraulic cylinder.

So that during an operation a sufficient amount of working fluid is available with no need to exchange the supply cylinder, a procedure that would involve a not inconsiderable interruption of the operation, the supply cylinder must have a relatively large volume. The larger the cylinder bore is made, the larger must be the force exerted by the hydraulic system, and hence a correspondingly greater stability is required of the receptacle for the supply cylinder. On the other hand, if the volume of the supply cylinder is increased by lengthening it, and hence lengthening the stroke of the piston, the result is an increase in the overall height of the appliance. The present-day compromise has produced supply cylinders with a diameter of ca. 60 mm, with the result that the associated appliances are constructed as stands and have a height of ca. 1,200 to 1,500 mm. The necessary actuation devices, i.e. the hydraulic cylinder along with the associated hydraulic pump, are extremely elaborate and very awkward to use.

Furthermore, in the case of "small" operations for which only a slight amount of fluid is used, the excess working fluid must be discarded because of the sterility requirements for a working fluid, which increases the operating costs of the known appliance.

SUMMARY

It is the object of the disclosed embodiments to provide a simple appliance that enables economical operation while reducing the structural complexity.

According to the disclosed embodiments there is provided an appliance for water-jet surgery including a plurality of supply cylinders, each supply cylinder including a piston, a working fluid enclosed therein, and an outlet, wherein the working fluid is enclosed within each supply cylinder in a leak proof manner until it is caused to be expelled, by means of the piston, through the outlet; a pressure conduit in fluid communication with the outlet of each of the plurality of supply cylinders and into which the working fluid is expelled. At least one actuation device is provided to actuate the pistons. In addition, a change-over device is provided to shift the actuation from a first piston corresponding to a first plurality of supply cylinders to a second piston corresponding to a second plurality of supply cylinders such that the working fluid can be expelled into the pressure conduit from the supply cylinders one after another, as they are consecutively emptied.

The single supply cylinder previously provided in the disclosed embodiments is subdivided into a plurality of correspondingly smaller supply cylinders. This measure solves several problems simultaneously. First, because of their reduced diameter the smaller supply cylinders can be made of a weaker material, which nevertheless can resist the prevailing high pressures. Second, the required working pressure can be produced with less force, so that the necessary actuation devices can be more simply constructed. Third, the appliance can be made very much smaller, e.g., can be set onto a table, on account of the smaller stroke of the pistons. And fourth, during a "relatively small" operation fewer supply cylinders are used up than in a "larger" operation; in the present appliance, the supply cylinders that have not been used are available for a subsequent operation, as their sterility is still ensured.

Preferably the change-over device is constructed so that there is some overlap between the consecutive periods during which pistons are actuated, so that the expulsion of fluid into the pressure conduit produced by their actuation is uninterrupted. Whereas on one hand, in the case of the conventional large-volume supply cylinders, such an uninterrupted supply of working fluid is ensured by the large fluid volume, with the disclosed embodiments this uninterrupted supply of fluid is very efficiently achieved.

Preferably sealing devices are provided to make the fluid outlet on the supply cylinder water-tight, so that no manual coupling is needed for a firm connection. Instead, a forceful automatic/mechanical coupling of the supply cylinder to the sealing device suffices.

An overlapping actuation of the pistons is especially simple when a plurality of actuation devices is provided. Then there is no need to move the actuation devices from one piston to the next. When the number of actuation devices corresponds to the number of supply cylinders in the device, a simple (electronic) control means can implement the change-over. However, it is also possible to work with a smaller number of actuation devices (only one, in the minimal case) if the change-over device ensures that the actuation device is always guided to the next in a sequence of new supply cylinders.

The pistons are preferably provided with back-flow barriers, such that after working fluid has been ejected by a piston, the piston cannot be pushed back into a previous position from the position it has reached, in particular from its final position after all the working fluid has been ejected. By this means it can be ensured that refilling is prevented and hence the possibility of working with unsterile medium can be reliably eliminated.

At the outlet of the supply cylinder an irreversibly openable transport gasket is preferably provided. This measure likewise makes it possible for the use of unsterile medium to be prevented. Furthermore, such an irreversibly openable transport gasket can be very simply constructed and designed in such a way that it opens automatically when a supply cylinder is put into place or when it is first actuated. Because of the very high pressures employed here, it is possible also to construct the transport gasket so that it opens automatically when pressure is first applied.

Preferably a change-over magazine is provided, which accommodates a group of supply cylinders. This makes handling of the apparatus particularly simple, both during the insertion of multiple supply cylinders into the appliance and when individual actuation devices are being changed over from one supply cylinder to another. The change-over magazine preferably comprises chambers that closely surround the supply cylinders. In this case the supply cylinders can be constructed with an especially thin wall, which expands somewhat as the pressure builds up and then becomes apposed to the walls of the change-over magazine. The receptacle can also be made with sufficient shape stability to withstand the pressure without becoming form-fitted to the housing.

In the change-over magazine collection devices are preferably provided, to guide the working fluid from several supply cylinders to the pressure conduit. This is especially advantageous when the working fluid is being conducted in an overlapping manner from various supply cylinders.

Preferably ventilation devices are provided, in particular to remove air simultaneously from conduit sections between the outlets of the supply cylinders and the pressure conduit, so that there is no interruption or pulsation of the working fluid associated with the release of air remnants. Preferably the ventilation devices are disposed in the change-over magazine.

In one disclosed embodiment the change-over magazine is fixedly connected to the pressure conduit and is intended to be used only once. In this case the change-over magazine can already be filled with supply cylinders by the manufacturer, so that although the advantage of saving working liquid (as well as the supply cylinders) is no longer obtained, all the other advantages cited above are nevertheless preserved. A special advantage in this case is the ease of manipulation, in particular with regard to sterility criteria.

BRIEF DESCRIPTION OF THE DRAWINGS

The foregoing summary, as well as the following detailed description of the disclosed embodiments, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION

Figure 1:
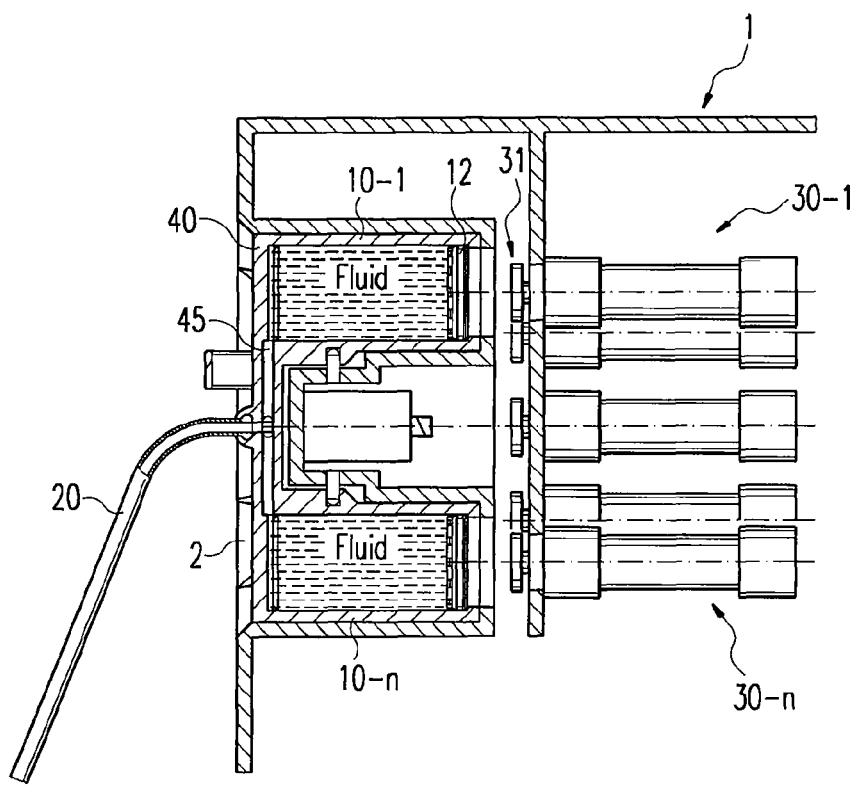
FIG. 1 is a schematic sectional drawing of one disclosed embodiment with inserted magazine, prior to actuation.
Figure 2:
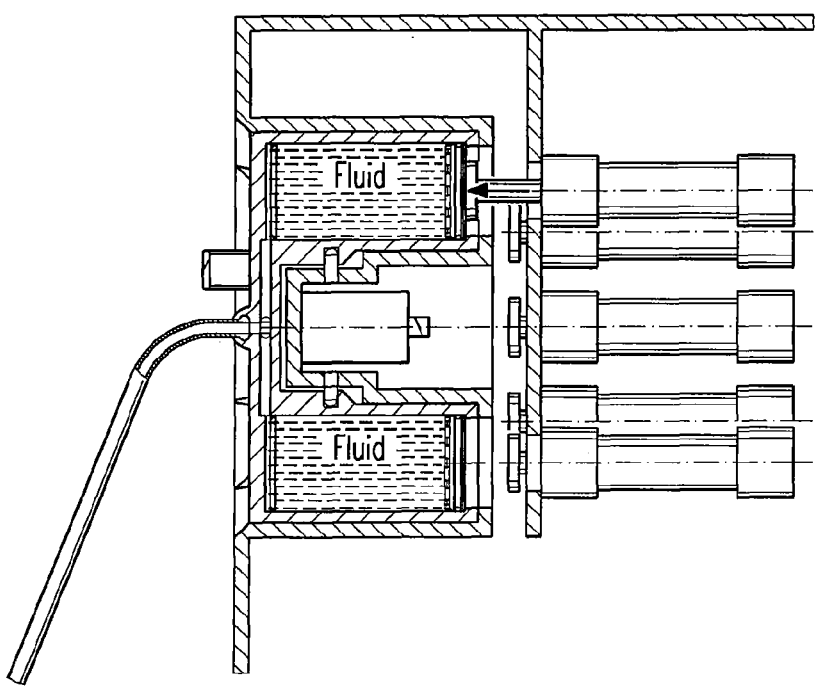
FIG. 2 shows the arrangement according to FIG. 1 during the initial phase of actuation of one cylinder.

In the following description, the same reference numerals are used for identical parts or parts with identical actions.

In the first disclosed embodiment, shown in FIGS. 1-5, an appliance housing 1 is provided that comprises an opening 2 on its front side, into which a change-over magazine 40 can be inserted.

The change-over magazine 40 contains a plurality of supply cylinders 10-1 to 10-$n$; in the embodiment shown here, there are 8 such supply cylinders 10. It is evident in the drawings that in this case the supply cylinders 10 have been constructed directly within the change-over magazine or are formed by the magazine itself, and have not been inserted as separate cylinders.

Each of the supply cylinders 10 comprises a piston 12 that closes the cylinder at one end. In the interior of the supply cylinders 10 a working fluid 11, in particular Ringer solution, is enclosed in a leakproof manner.

Each supply cylinder communicates with an outlet 13 having a collection channel 45, which in turn is connected to a pressure conduit 20.

Figure 4:
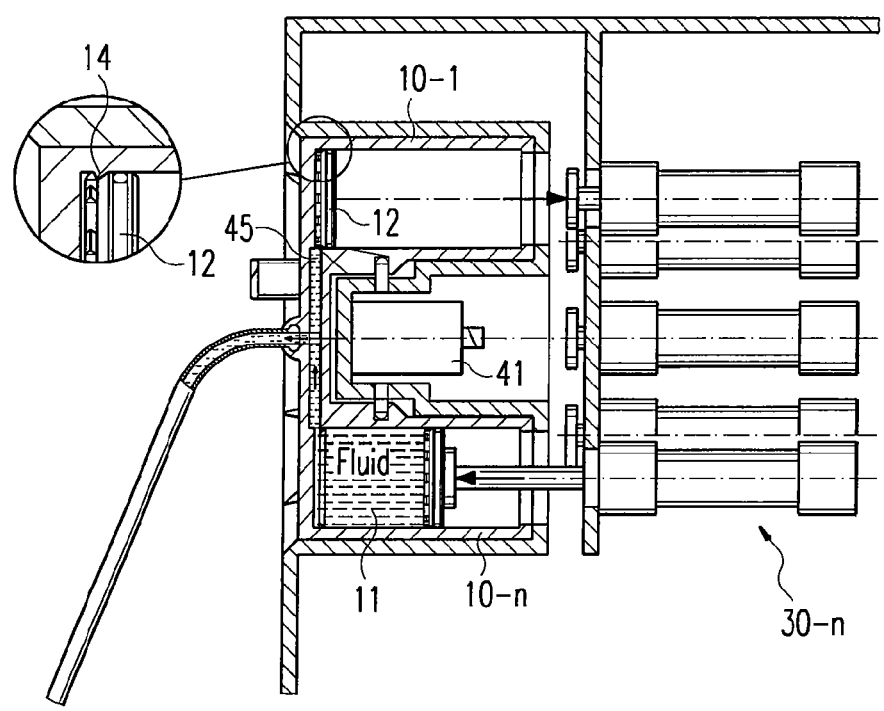
FIG. 4 shows the previously illustrated arrangement when one supply cylinder is empty and another supply cylinder is being actuated.
Figure 5:
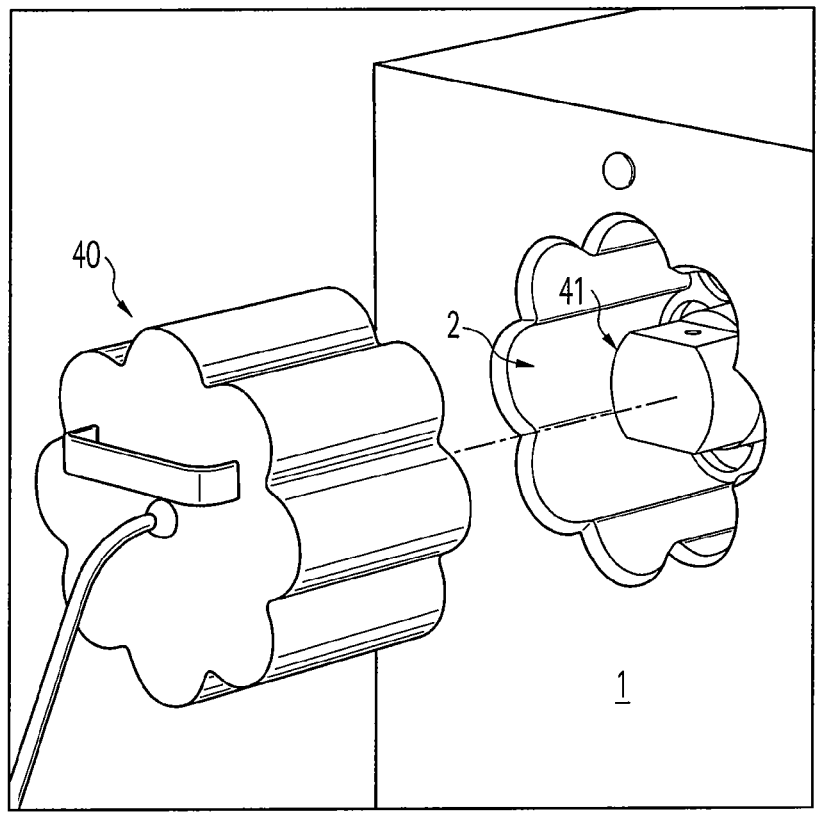
FIG. 5 is a perspective drawing of part of the arrangement according to FIGS. 1-4.

The pistons 12 comprise—as shown in the enlarged section of FIG. 4—a back-flow barrier 14 that keeps the piston 12 in its final position, i.e. when all the fluid has been expelled, as is known per se for single-use syringes.

After being inserted into the opening 2 of the housing 1 (see FIG. 5), the change-over magazine 40 is locked to a holder 41, so that it is firmly retained within the appliance housing 1.

Within the housing 1 there are additionally provided actuation devices 30-1 to 30-$n$, which are shown here as hydraulic cylinders but can of course also be designed as electrically driven recirculating ball screws or the like.

Each of the actuation devices 30 comprises a plunger 31, which is disposed in the housing 1 in such a way that when the change-over magazine 40 is in position, the actuating plungers 31 are situated opposite the pistons 12 that face them.

The insertion position, i.e. the position of the components immediately after the change-over magazine 40 has been inserted into the housing 1, is shown in FIG. 1. In this position the collection channel 45 and the pressure conduit 20 are still empty.

Figure 3:
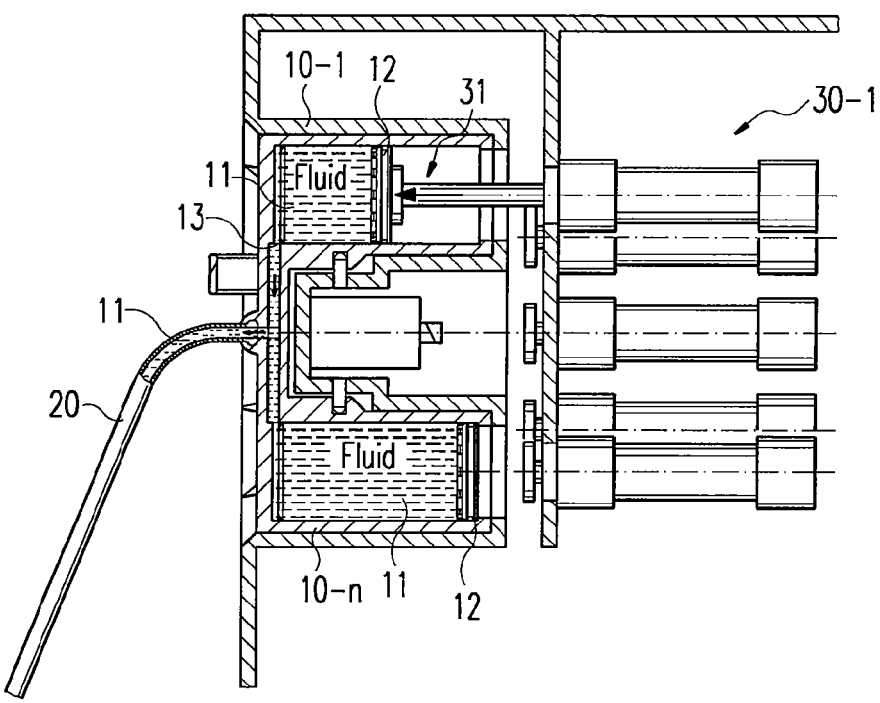
FIG. 3 shows the previously illustrated arrangement during the expulsion of working fluid.

Now when the first actuation device 30-1 is actuated, so that its plunger 31 is driven forward, the plunger—as shown in FIG. 3—presses the piston 12 into the supply cylinder 10, so that fluid 11 passes through an outlet 13 of the first supply cylinder 10-1 into the collection channel 45 and through the latter into the pressure conduit 20, which conducts it to the working instrument (not shown).

As soon as the first supply cylinder 10-1 is empty (see FIG. 4), another supply cylinder 10-$n$ is "triggered" to deliver its stored working fluid 11 by way of the plunger 31 of the associated actuation device 30-$n$. As this occurs, the piston 12 of the emptied supply cylinder 10-1 is retained in its final position by the back-flow barrier 14, so that any force exerted by fluid emerging from the supply cylinder 10-$n$ and present in the collection channel 45 cannot cause this piston 12 to be pushed backward.

Figure 6:
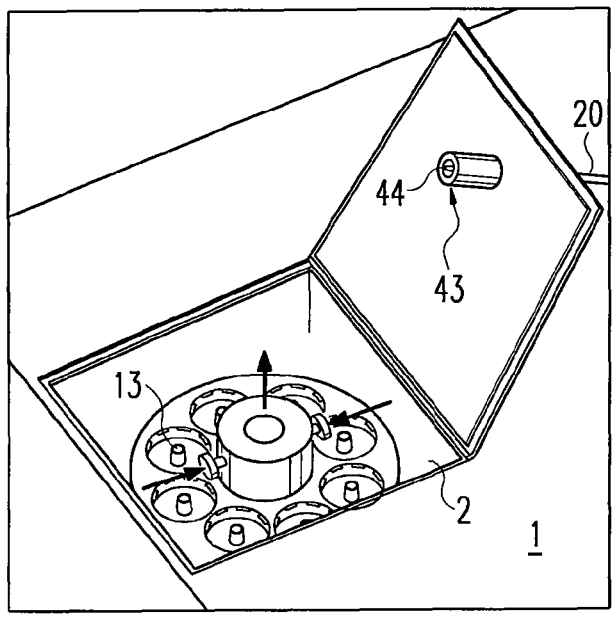
FIG. 6 is a perspective drawing of part of another embodiment.
Figure 7:
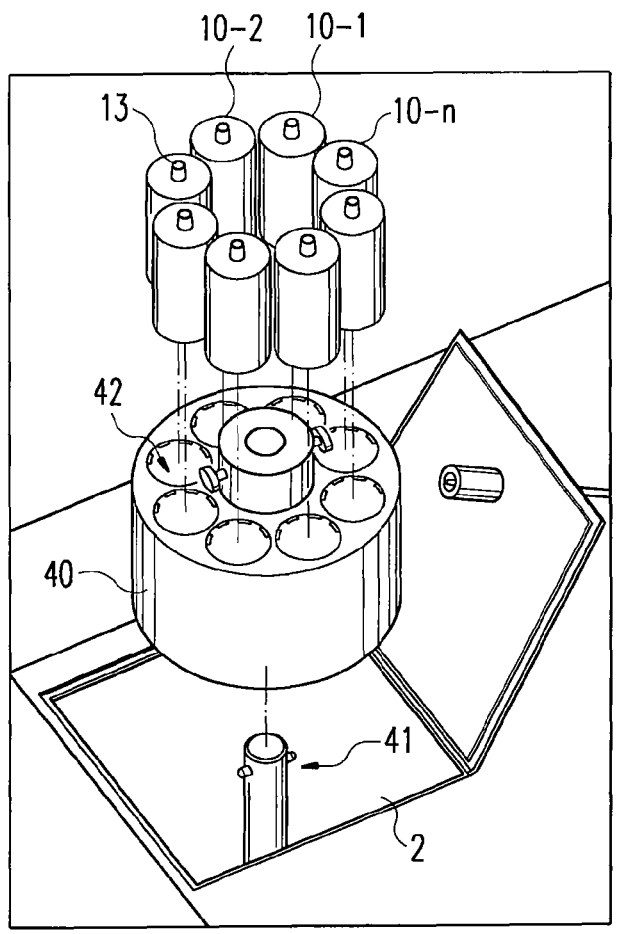
FIG. 7 is an exploded drawing of part of the arrangement according to FIG. 6.

The embodiment shown in FIGS. 6 and 7 differs from that according to FIGS. 1-5 in particular in that the change-over magazine 40 comprises chambers 42 into which individual supply cylinders 10 can be inserted as separate "structural components". In this arrangement the changeover magazine 40 can be rotated about its axis, allowing supply cylinders 10-1 to 10-$n$ to be consecutively positioned so that their outlet 13 is connected to a sealing device 43, which mediates a leakproof connection between the associated supply cylinder 10 and the pressure conduit 20. These drawings show an opening needle 44, which is provided to open closure devices (not shown) on the outlets 13 of the supply cylinders 10; this needle opens the closure device of the relevant supply cylinder 10 whenever the sealing device 43 is pressed against the outlet 13 of the supply cylinder 10. Exchanging of the supply cylinders 10 by rotation of the B-change-over magazine 40 thus corresponds somewhat to the replacement of cartridges in (or at the entrance to) the barrel of a revolver.

Figure 8:
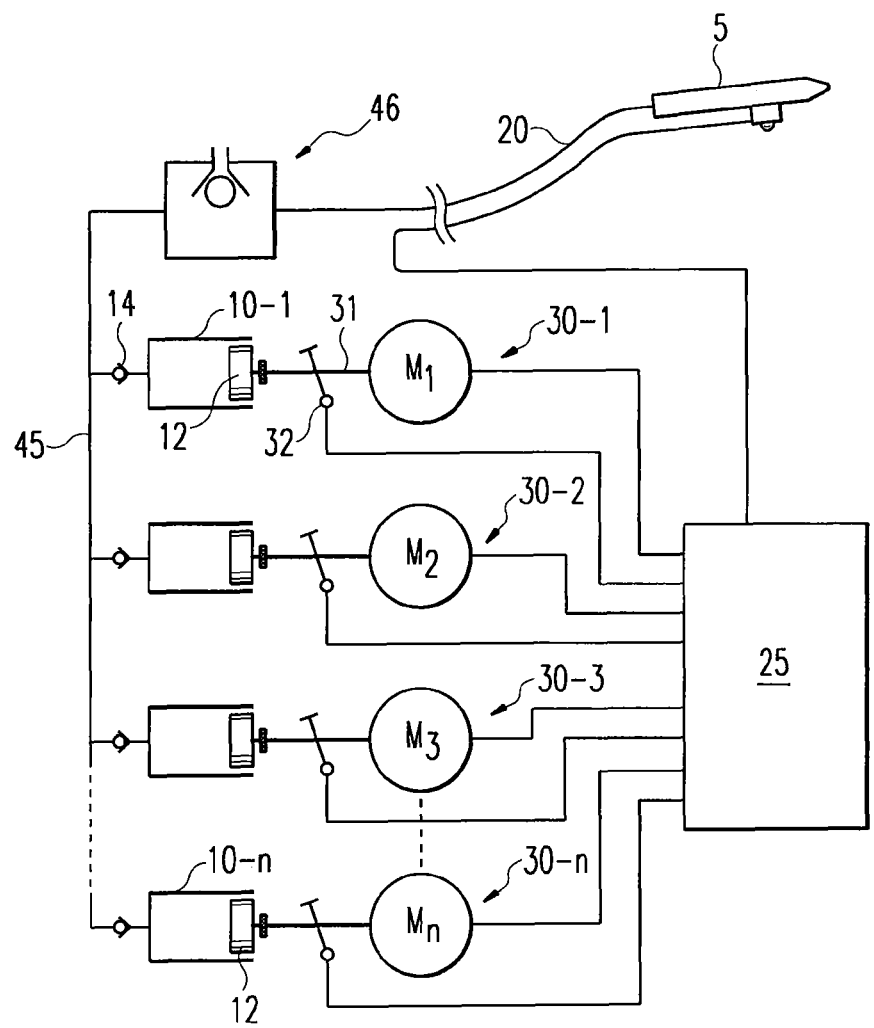
FIG. 8 is a schematic drawing of a control means for the arrangement according to FIGS. 1-5.

FIG. 8 shows a—highly schematic—control means for the appliance according to FIGS. 1-5.

This control means comprises a computer 25 that is in controlling communication with the actuation devices 30-1 to 30-$n$. The plungers 31 of the actuation devices 30-1 to 30-$n$, which in the present case are constructed as electromotor drives (e.g., with recirculating ball screws), exert pressure on the pistons 12 of the supply cylinders 10. The force thus employed can in this embodiment be controlled by the current with which the electromotors $M_1$-$M_n$ are driven by the computer 25.

The outlets of the supply cylinders 10 are connected to the collection channel 45. Between the various supply cylinders 10 and the collection channel 45 are provided back-flow barriers 14, here constructed as back-flow valves, disposed in such a way that the pressure in the collection channel 45 can in no case have an effect on a piston 12 that at the moment is not being actuated with the corresponding force.

Between the collection channel 45 and the pressure conduit 20 leading to a working instrument 5, a ventilation device 46 is provided.

In addition path sensors 32 are provided, which send a signal to the computer 25 at least when the associated plunger 31 has reached its final position.

With the arrangement shown in FIG. 8 it is now possible to drive the actuation devices 30-1 to 30-$n$ in such a way that the supply cylinders can be emptied one after another, and even in such a way that their emptying periods overlap, so that the operator is not disturbed by fluctuations in pressure of the working fluid.

From the above it will be evident that a combination of the individual characteristics explained here is readily possible. For example, the magazine shown in FIGS. 6 and 7 can also be replaced by one according to FIG. 5 (to be used only once). Control by the computer 25 shown here can of course be replaced by provision of a corresponding cam-disk mechanism.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An appliance for water jet surgery, comprising:
   a working instrument having a nozzle;
   a plurality of single-use supply cylinders, each supply cylinder including a side wall, a piston, a working fluid, and an outlet, wherein the working fluid is enclosed within each supply cylinder in a leak proof manner until it is caused to be expelled, by means of the piston, through the outlet;
   wherein each piston comprises a back-flow barrier such that, after the piston has reached a position in which the working fluid has been expelled from its associated supply cylinder, the piston cannot be pushed back into a previous position, and/or
   an irreversibly openable transport gasket is provided at the outlet of each supply cylinder;
   a single pressure conduit in fluid communication with the outlet of each of the plurality of supply cylinders and into which the working fluid is expelled, the single pressure conduit being connected to the nozzle of the working instrument;
   at least one actuation device to actuate the pistons;
   a change-over device to shift the actuation from a first piston corresponding to a first of the plurality of supply cylinders to a next piston corresponding to a next of the plurality of supply cylinders such that the working fluid can be ejected into the single pressure conduit from consecutively emptying supply cylinders; and
   a change-over magazine that receives the plurality of supply cylinders,
   wherein the change-over magazine defines chambers, each of which receives and closely surrounds the side wall of the respective one of the plurality of supply cylinders.

2. The appliance according to claim 1, wherein the change-over device operates such that consecutive actuation periods of each of the pistons overlap one another in order that expulsion of the fluid into the single pressure conduit is uninterrupted.

3. The appliance according to claim 1, wherein a sealing device is provided to provide a leak proof connection to each fluid outlet.

4. The appliance according to claim 1, comprising a plurality of actuation devices.

5. The appliance according to claim 1, wherein the change-over magazine further comprises collection devices to conduct working fluid from the plurality of supply cylinders to the single pressure conduit.

6. The appliance according to claim 1, further comprising ventilation devices for the removal of air from conduit sections located between the outlets of the plurality of supply cylinders and the single pressure conduit.

7. The appliance according to claim 6, wherein the ventilation devices are disposed in a change-over magazine.

8. The appliance according to claim 1, wherein the change-over magazine is irreversibly connected to the pressure conduit to form a single-use unit.

9. The appliance according to claim 1, wherein the plurality of supply cylinders are arranged in the change-over magazine around a central axis of the change-over magazine.

10. The appliance according to claim 9, wherein the plurality of supply cylinders are arranged parallel to the central axis of the change-over magazine.

11. The appliance according to claim 9, wherein the change-over magazine rotates around the central axis.

12. The appliance according to claim 1, wherein each of the plurality of supply cylinders is individually replaceable.

13. The appliance according to claim 1, wherein the plurality of supply cylinders is integrally formed in the change-over magazine.

* * * * *

UNITED STATES PATENT AND TRADEMARK OFFICE
CERTIFICATE OF CORRECTION

PATENT NO.       : 8,679,143 B2  
APPLICATION NO. : 10/599672  
DATED            : March 25, 2014  
INVENTOR(S)      : Kuehner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 930 days.

Signed and Sealed this

Twenty-ninth Day of September, 2015

Michelle K. Lee
*Director of the United States Patent and Trademark Office*